United States Patent [19]

McCurdy

[11] 4,077,394

[45] Mar. 7, 1978

[54] INTEGRAL PRESSURE SENSOR PROBE FOR A CARDIAC ASSISTANCE DEVICE

[76] Inventor: Martin D. McCurdy, 759 E. Foothill, Glendora, Calif. 91740

[21] Appl. No.: 717,493

[22] Filed: Aug. 25, 1976

[51] Int. Cl.² .................... A61B 19/00; A61M 1/03
[52] U.S. Cl. ........................ 128/1 D; 128/2.05 D
[58] Field of Search ........... 128/1 D, 2 M, 2.05 D, 128/344, 348, 349 B, 214

[56] References Cited

U.S. PATENT DOCUMENTS

| 3,581,733 | 6/1971 | Grandjean | 128/2.05 D |
| 3,585,983 | 6/1971 | Kantrowitz et al. | 128/1 D |
| 3,610,228 | 10/1971 | Temkin | 128/2.05 D |
| 3,675,891 | 7/1972 | Reynolds et al. | 128/214 F X |
| 3,692,018 | 9/1972 | Goetz et al. | 128/1 D |

*Primary Examiner*—Dalton L. Truluck
*Attorney, Agent, or Firm*—Boniard I. Brown

[57] ABSTRACT

A pressure sensor probe is disclosed whose pressure interface forms the extreme end of a balloon type cardiac assistance device, hydraulic interface usually being provided to feed the pressure within a patient's aorta back to a sensor outside the patient. A small tube provides the inter-connection between the interface of blood and sensing solution and the sensor which tube enters the tubular conduit used to feed pneumatic pressure to the balloon at an intermediate position thereof and extends therethrough toward the patient.

7 Claims, 7 Drawing Figures

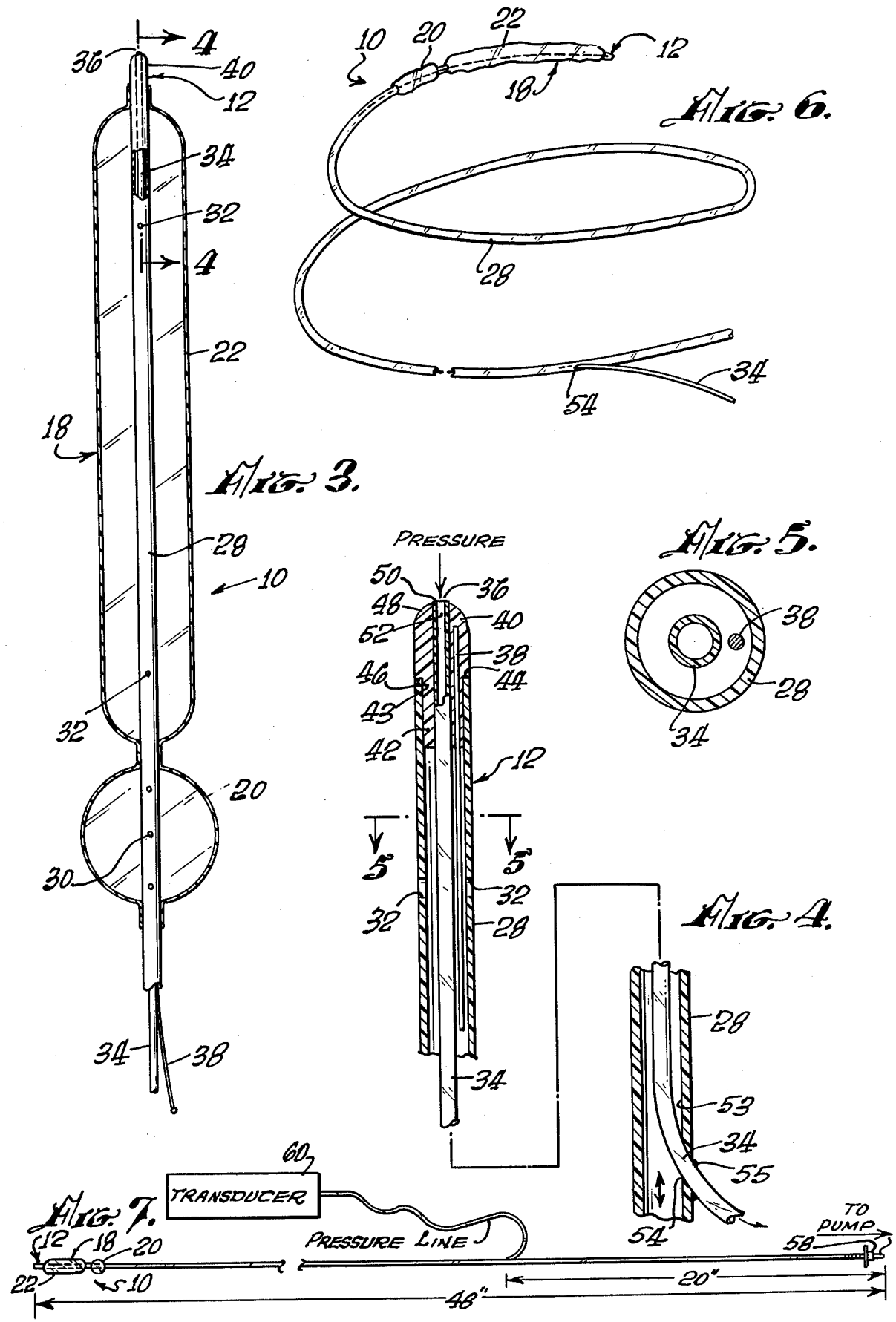

INTEGRAL PRESSURE SENSOR PROBE FOR A CARDIAC ASSISTANCE DEVICE

CROSS REFERENCE TO RELATED PATENTS

This application relates to the subject matter of U.S. Pat. No. 3,675,891 entitled Continuous Catheter Flushing Apparatus by Gordon S. Reynolds et al. and U.S. Pat. No. 3,692,018 entitled Cardiac Assistance Device by Robert H. Goetz, and reference is made to the information therein as though fully set forth hereinbelow.

BACKGROUND OF THE INVENTION

A common death causing failure of mammals such as human beings is a heart failure caused by occlusion of the coronary arteries of the heart. An occlusion in the coronary artery reduces the flow of blood to the heart muscle which loses its contractibility and hence, its pumping capacity. The victim then goes into cardiogenic shock whereby the heart progressively loses its ability to pump blood. This progressive loss of pumping ability occurs because the heart receives its blood supply through the coronary arteries only during its resting phase. When there is a blockage and an area of the heart muscle loses its ability to pump, the victim's systolic and diastolic blood pressures are reduced. The diastolic pressure is that pressure maintained in the arteries during the time that the heart is resting and is what causes blood to flow through the coronary arteries to nourish the heart. Since the weakened heart during an attack causes the diastolic pressure to be below its normal point, the heart receives less and less nourishment which causes more and more area of the heart muscle to be involved in the attack. This cumulative process if unchecked causes death when the heart can no longer sustain itself.

It should be noted that in most cases of coronary occlusion, sufficient heart muscle remains to pump some blood although it may not be an adequate blood flow to prevent cardiogenic shock. A device to assist the heart during this critical period is desirable, an example of which is the balloon type pneumatic pumping machine produced by the Datascope Company of Saddle Brook, New Jersey and described in U.S. Pat. No. 3,692,018. In this device a properly sized inflatable balloon is inserted into the patient's arterial system through an incision made in the groin. The balloon is then fed upwardly through the femoral artery to the aorta and maintained in position just below the carotid arteries. Through the use of EKG signals and appropriate controls, the balloon is caused to inflate and contract, to counter-pulsate the heart. This withdraws or receives blood from the left ventricle of the heart during systole and injects or replaces blood into the aorta during diastole. To make the proper adjustments to this pulsation cycle, the blood pressure of the victim must be sensed and compared as the various controls on the Datascope device are adjusted. The blood pressure is normally sensed by inserting a tube into a wrist artery. This common procedure has many disadvantages; the most important of which being that at a very critical time, where no time should be wasted, it can take as much as 20 minutes to perform. Pressure sensing tubes in such wrist arteries are not desirable for other reasons as well. They tend to cause clots because of their large relative size to the blood flow thereabout and therefor must be replaced or moved every two to three days. Also, the pressure sensed is not the pressure in the aorta but some different pressure that is attenuated and phased by the arterial tree between the aorta and the wrist. If the desired aorta pressure data was available, such also could be used to assure proper positioning of the ballon before the Datascope device is activated, thus reducing the changes that it is activated with a portion of the balloon in a carotid artery, which might kill the patient. Therefore, there has been a continuing need to provide means to sense the aorta pressure which do not tend to clog, which take no time to insert and which remain accurate over an extended length of time. It has also been desired to provide means to assure a doctor that he is inserting the aforementioned ballon in the correct position within the aorta.

BRIEF DESCRIPTION OF THE PRESENT INVENTION

The present invention solves all of the aforementioned problems by providing a pressure sensing probe which is integral with the cardiac assistance ballon so that the probe for pressure sensing means is inserted along with the ballon. The probe includes a small tube which opens at the outermost extremity of the ballon. The tube runs within at least a portion of a larger pneumatic conduit and is connected to a sensor outside of the patient's body. The larger pneumatic conduit is used to inflate and deflate the balloon. All parts of the probe which are inserted within the patient have nonthrombogenic exteriors to prevent the occurrence of blood clots. The sensor tube is normally filled with a saline solution of a pressure equal to the blood pressure so that there is a relatively stable blood/saline interface at the open end of the tube. Blood pressure sensors of suitable type are manufactured by various companies including Bell and Howell. The sensor tube preferably exits the pneumatic conduit at an intermediate location thereof which is outside the patient. This allows shortening of the pneumatic conduit when the facilities so permit for improved pneumatic response without interference with the pressure sensing means.

It should be obvious that since the blood/saline interface of the pressure sensing means is at the outermost extremity of the ballon which is facing the heart and is in the aorta, the pressure sensed thereat is actual aorta pressure with minimum attenuation and phase delay. Since the blood flow around this area is relatively great and the exterior of the device is constructed for non-thrombogenic material, the problem of blood clots is lessened, and since the probe is inserted along with cardiac assist ballon, no extra time is taken up in the insertion of separate pressure sensor means. Since actual aorta pressure is measured, the pressure indications of the pressure sensor can be used by the doctor as he is inserting the cardiac assist ballon to assure himself that he has not inadvertently inserted the balloon too far where it tends to go up into and block a carotid artery.

It is therefore an object of the present invention to provide an integral pressure sensing probe for a ballon type cardiac assistance device.

Another object of the present invention is to reduce the time required to provide assistance to a patient in cardiac distress.

Another object is to provide pressure sensing means which can operate within a receiver of cardiac assistance over long periods of time without removal or replacement.

Another object is to provide an integral pneumatic ballon and hydraulic pressure sensing probe which does not interface with "on the spot" shortening of the pneumatic conduit to improve the operation of the overall system, especially during high heart rates.

Another object is to provide pressure sensing means for assisting the doctor in properly locating a balloon type cardiac assistance device within a patient.

These and other objects and advantages of the present invention will become apparent to those skilled in the art after considering the following detailed specification which covers the preferred embodiment thereof in conjunction with the accompanying drawings.

BRIEF DESCRIPTION OF THE DRAWINGS

FIG. 3 is a partial cross-sectional view of the integral cardiac assistance ballon and pressure sensing probe of the present invention;

FIG. 4 is an enlarged cross-sectional view taken at line 4—4 of FIG. 3;

FIG. 5 is an enlarged cross-sectional view taken at line 5—5 of FIG. 4;

FIG. 6 is a view of the pneumatic conduit and pressure sensing tube with a collapsed balloon on the end thereof; and FIG. 7 is a partially cutaway view of the device of FIG. 6 showing typical dimensions for the entry point of the pressure sensor tube into the pneumatic conduit.

DETAILED DESCRIPTION OF THE SHOWN EMBODIMENT

Figure 1:
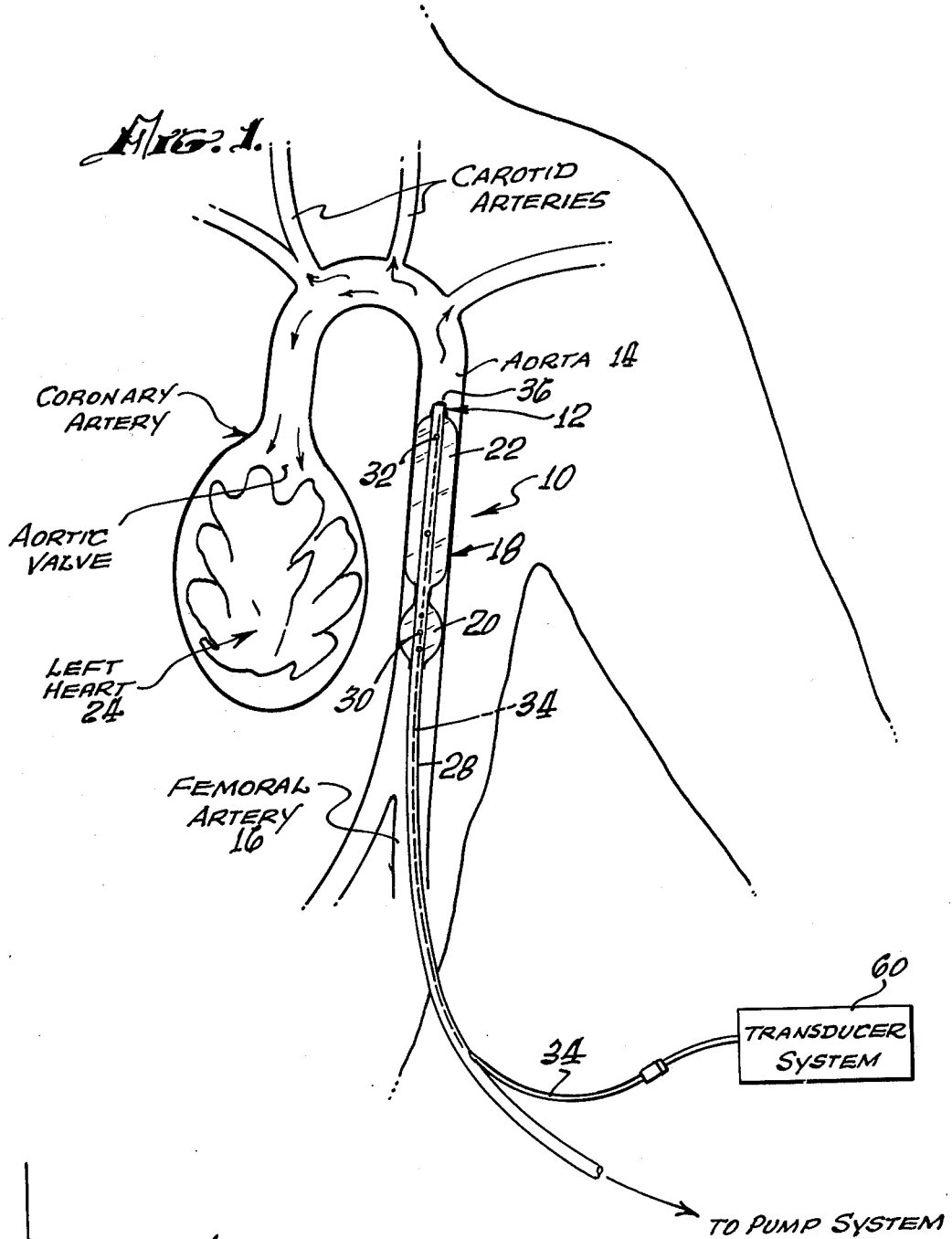
FIG. 1 is a partial cross-sectional view of a cardiac assistance device employing the pressure sensor probe of the present invention disposed within the aorta of a human patient.
Figure 2:
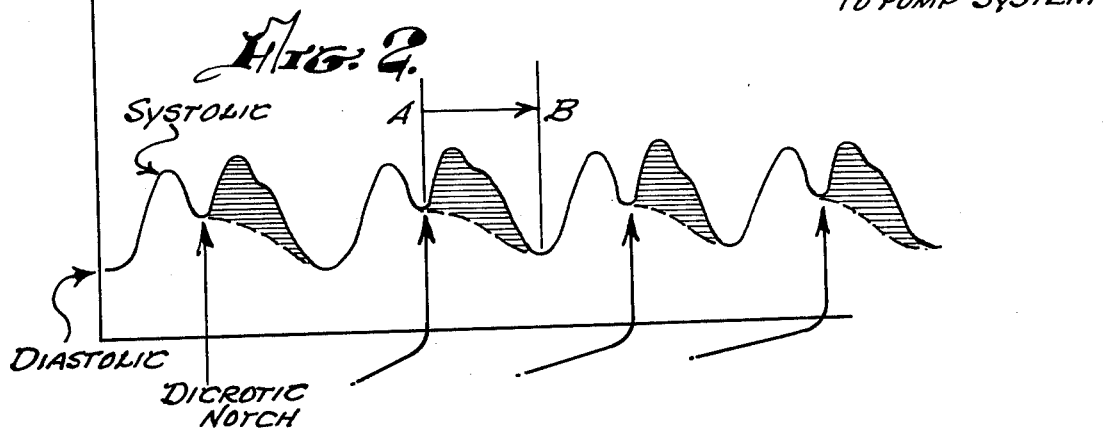
FIG. 2 is a plot of a typical patient's aorta blood pressure while he is receiving cardiac assistance from a device such as shown in FIG. 1.

Referring to the drawings, more particularly by reference numbers, number 10 in FIG. 1 refers to a cardiac assistance device having a pressure probe 12 constructed and located according to the present invention. As shown the assistance device 10 has been inserted within the aorta 14 of a patient by suitable surgical procedures which usually include insertion through the femoral artery 16 at the groin of the patient. The cardiac assistance device includes a ballon 18 which typically has first and second chambers 20 and 22. The chamber 20 inflates first to occlude the aorta, thereafter the second chamber 22 inflates to pressurize the blood trapped between the chamber 20 and the heart 24. This causes the blood to flow away from the point of occlusion and toward the coronary and carotid arteries. The inflation process for the ballon 18 is preferably commensed upon sensing the dicrotic notch in the blood pressure. This is shown in FIG. 2 wherein a dashed line is used to show normal unassisted blood pressure with a shaded area thereabove showing the blood pressure increase caused by the cardiac assistance device 10. The provide the most assistance for the heart the ballon 18 should inflate just as the dicrotic notch is created by the closing of the aortic valve. The ballon 18 should also collapse just in time for the heart 24 to contract on its next beat. Therefore assistance to the heart 24 is provided during the time indicated by the arrow from A to B in FIG. 2.

The information required to properly inflate and deflate the ballon 18 only can be acquired partially from the EKG of the patient. What the technician needs to properly adjust the device 10 is a aortic blood pressure reading such like that shown in FIG. 2.

The ballon 18 with its to chambers 20 and 22 is shown in detail in FIG. 3. As can be seen, pneumatic conduit 28 is used to communicate a fluid medium such as air under pressure with the two chambers 20 and 22 through holes 30 and 32 provided for that purpose. The probe 12 of the present invention is provided by running a small tube 34 within the conduit 28, the open end of the tube 34 extending to the outermost extremity of the ballon 18. The tube 34 can be attached to any suitable pressure sensor in conjunction with a continuous flush system of the type manufactured by the Sorenson Research Company wherein a saline blood interface is maintained at the tip 36 of the tube 34. A stiffener wire 38 which is relatively opaque to X rays is usually included along at least a portion of the tube 34 within the conduit 28 to make insertion of the assembly relatively easy. The wire 38 is normally maintained in proper position by being molded into a tip member 40 as shown in FIG. 4, which includes a flange 42 which is inserted within the end 43 of the conduit 28 with the tip 44 of the condut 28 in abutment with a suitable abutment surface 46 extending radially outward from the flange 42. The pressure sensing tube 34 extends through the tip member 40 so that the tip 36 is actually formed by a generally hemispherical surface 48 of the tip member 40 and the end surface 50 of the tube 34. A typical position of the interface 52 between the blood and saline solution is shown in FIG. 4. The relative coaxial position of the conduit 28 and the tube 34 can be seen in the cross-sectional view of FIG. 5 which also shows the position of the stiffener wire 38 with respect to the conduit 28 and the tube 34.

It is preferable that the tube 34 be brought out through the side wall 53 of the conduit 28 at a suitable position 54 and is sealed thereto by suitable sealent means 55. As shown in FIGS. 6 and 7, it is normally desirable that a substantial length of conduit 28 extend beyond the place 54 where the sensing tube 34 passes through the conduit side wall 53. This is because the physical layout of many facilities requires a relatively long conduit 28 so that it can be attached to the source of air pressure by means of connection 58 shown in FIG. 7. On the other hand, sometimes the heart rate of a patient makes it mandatory to shorten the conduit 28 since the pnuematic lag in a long conduit 28 is so great that the ballon 18 must be deflated to avoid a heart contraction prior to the time it should have been inflated. The shortening of the conduit 28 reduces the time required to inflate the ballon 18 and therefor provides a higher frequency response. As shown in FIG. 7 the pressure line 34 is normally connected to some sort of pressure transducer 60.

Thus there has been shown and described a novel blood pressure probe integral with the ballon of a cardiac assistance device which fulfills all the objects and advantages sought therefore. Many changes, modifications, variations, other uses and applications of the subject invention will, however, become apparent to those skilled in the art after considering the specification and the accompanying drawings. All such changes, modifications, alterations, other uses and applications that depart from the spirit and scope of the invention are deemed to be covered by the claims which follow.

What is claimed is:

1. A cardiac assistance device including a pump structure adapted to be inserted into a blood vessel of a patient having a conduit for conducting fluid medium into and out of the blood vessel and an expandable and contractile structure connected to said conduit for expansion and contraction in response to said fluid medium to pump blood within the vessel, the conduit having at least one wall and two ends, the first end being opposite from said expandable and contractile structure and being adapted to communicate with a source of pressurized fluid, the improvement comprising:

a pressure sensor probe which extends out of said conduit at its second end, said probe including a tube within at least a portion of said conduit, said tube having an outer diameter sized to fit loosely within said conduit without disrupting fluid medium flow therein, said tube having an open end adjacent the second end of said conduit and a second end adapted for connected to a pressure sensing device, and a tip member attached between said tube and said conduit and forming a seal therebetween.

2. The device defined in claim 1 wherein said tip member has an abutment surface for abutting the second end of said conduit and an adjacent flange which extends a predetermined distance within said conduit.

3. The device defined in claim 2 wherein said tube sealably extends through said conduit wall at a location between the two ends thereof so that a piece of conduit including said first end can be removed to shorten said conduit without cutting said tube.

4. The device defined in claim 2 wherein said tip member includes a stiffener member which extends therefrom between said conduit and said tube therewithin for a predetermined distance, said stiffener member being sized to allow relatively unimpeded flow of fluid medium within said conduit and outside said tube, said conduit defining at least one passageway through its wall for communication of the fluid medium to and from said expandable and contractile structure.

5. The device defined in claim 4 wherein said fluid medium is air, said tube being filled with liquid when said probe is in use.

6. The device defined in claim 4 wherein said tip member, said tube, said expandable and contractile structures and said conduit exteriors are constructed from nonthrombogenic material.

7. The device defined in claim 6 wherein said tip member includes a stiffener member which extends therefrom between said conduit and said tube therewithin, said stiffener member being constructed of a material which is relatively opaque to X-rays with respect to the other components of the device which are for insertion within the patient.

* * * * *